United States Patent
McCollough et al.

(10) Patent No.: US 9,879,824 B2
(45) Date of Patent: Jan. 30, 2018

(54) DEBRIS DETECTOR FOR NON-FERROUS BEARINGS

(71) Applicant: BELL HELICOPTER TEXTRON INC., Fort Worth, TX (US)

(72) Inventors: James M. McCollough, Arlington, TX (US); Ryan T. Ehinger, Irving, TX (US); Troy Bunch, Keller, TX (US)

(73) Assignee: Bell Helicopter Textron Inc., Fort Worth, TX (US)

( * ) Notice: Subject to any disclaimer, the term of this patent is extended or adjusted under 35 U.S.C. 154(b) by 759 days.

(21) Appl. No.: 13/863,126

(22) Filed: Apr. 15, 2013

(65) Prior Publication Data
US 2014/0305740 A1    Oct. 16, 2014

(51) Int. Cl.
| | | |
|---|---|---|
| *B01D 35/00* | (2006.01) | |
| *F16N 29/00* | (2006.01) | |
| *G01N 33/28* | (2006.01) | |
| *B64C 27/00* | (2006.01) | |
| *B64D 45/00* | (2006.01) | |
| *G01M 13/04* | (2006.01) | |

(52) U.S. Cl.
CPC .............. *F16N 29/00* (2013.01); *B64C 27/00* (2013.01); *B64D 45/00* (2013.01); *G01M 13/04* (2013.01); *G01N 33/2858* (2013.01); *G01N 33/2888* (2013.01)

(58) Field of Classification Search
None
See application file for complete search history.

(56) References Cited

U.S. PATENT DOCUMENTS

| | | | | |
|---|---|---|---|---|
| 3,980,560 A | * | 9/1976 | Eades | B01D 29/05 210/141 |
| 4,152,031 A | * | 5/1979 | Maguire | B62D 55/15 184/6.24 |
| 4,186,975 A | * | 2/1980 | Schwarz | B64C 27/54 384/465 |
| 5,604,441 A | | 2/1997 | Freese, V et al. | |
| 5,779,900 A | * | 7/1998 | Holm | B01D 29/15 210/411 |
| 5,968,371 A | * | 10/1999 | Verdegan | F01M 1/16 184/108 |

(Continued)

FOREIGN PATENT DOCUMENTS

| | | |
|---|---|---|
| EP | 0126554 | 11/1984 |
| EP | 0159094 | 10/1985 |
| GB | 2195263 | 4/1988 |

OTHER PUBLICATIONS

European Search Report dated Jul. 1, 2013 from counterpart EP App. No. 13166913.7.

(Continued)

*Primary Examiner* — Richard Gurtowski
(74) *Attorney, Agent, or Firm* — James E. Walton

(57) ABSTRACT

A system and method to detect non-ferrous debris from a non-ferrous roller bearing element. The system includes a trap in fluid communication with a lubrication fluid of the non-ferrous bearing and a sensor operably associate with the trap. The method includes trapping the non-ferrous material debris in the lubrication fluid with the trap and triggering the sensor upon detection of the non-ferrous material debris trapped within the trap.

18 Claims, 5 Drawing Sheets

(56) References Cited

U.S. PATENT DOCUMENTS

| | | | | |
|---|---|---|---|---|
| 6,165,355 | A | * 12/2000 | Coulonvaux | B01D 29/114 137/545 |
| 2006/0180132 | A1 | * 8/2006 | Zhao | F02M 25/06 123/574 |
| 2012/0067671 | A1 | * 3/2012 | Sammataro | F16N 29/04 184/6.4 |

OTHER PUBLICATIONS

European Office Action dated Jul. 24, 2013 from counterpart EP App. No. 13166913.7.
European Office Action dated Oct. 28, 2013 from counterpart EP App. No. 13166913.7.

* cited by examiner

DEBRIS DETECTOR FOR NON-FERROUS BEARINGS

BACKGROUND

1. Field of the Invention

The present application relates generally to debris detector systems, and more specifically, to a debris detector system configured to detect non-ferrous debris in a fluid lubrication system.

2. Description of Related Art

Roller bearings are well known in the art and are effective means for facilitating movement between to joined members. Conventional roller bearings are typically manufactured with high strength metals to compensate for forces exerted thereagainst during use. It should be understood that the roller bearings eventually wear and fail after much use, and the process of inspecting failure of the bearings is time consuming and expensive.

Roller bearings typically utilize a lubrication system, which is used to determine bearing failure. For example, a conventional debris detector is provided with a magnet that collects metal debris of the failed bearing in the lubrication fluid stream. An indicator notifies the user of metallic debris detection in the lubrication fluid stream, and the bearing is replaced shortly thereafter.

Recent developments in roller bearing designs are switching from metallic materials to non-ferrous materials. As explained, conventional debris detection systems utilize magnets or other suitable means to detect metallic materials in the fluid stream, thus are not adapted to detect non-ferrous materials. Therefore, conventional detection systems are not effective means to determine wear and failure of the roller bearings.

Although the foregoing developments in the field of debris detectors represent great strides, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
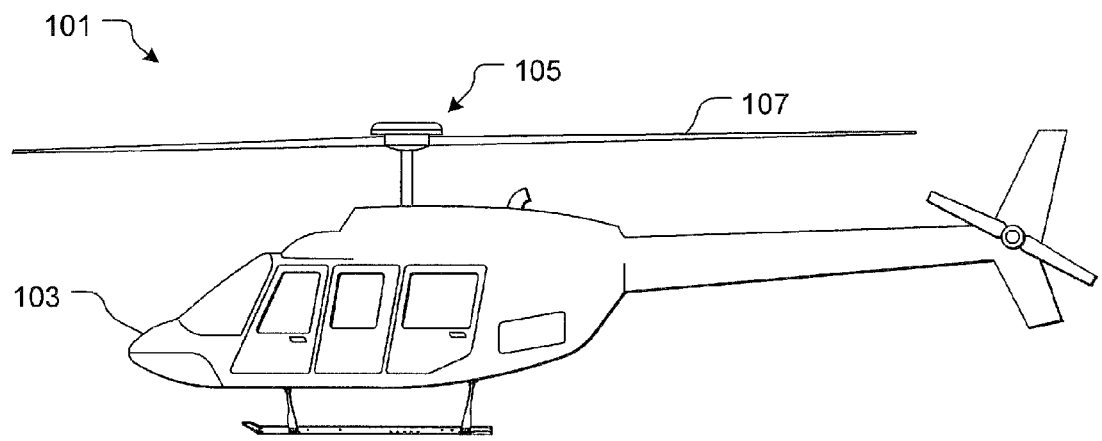
FIG. 1 is a side view of a helicopter according to a preferred embodiment of the present application.

While the system and method of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the apparatus and method are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system of the present application overcomes the abovementioned problems commonly associated with conventional debris detection systems. Specifically, the system of the present application includes a trap configured to collect non-ferrous material from a stream of lubrication fluid in communication with the roller bearing element. The system is further provided with a sensor operably associated with the trap and configured to sense the presence of the non-ferrous debris. It will be appreciated that the detection system provides easy and rapid diagnosis of bearing failure and can be retrofitted on existing roller bearing systems. Further detailed description of these features are provided below and illustrated in the accompanying drawings.

The system and method of the present application will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

Referring now to the drawings wherein like reference characters identify corresponding or similar elements throughout the several views, FIG. 1 depicts an aircraft 101 in accordance with a preferred embodiment of the present application. In the exemplary embodiment, aircraft 101 is a helicopter having a fuselage 103 and a rotor system 105 carried thereon. A plurality of rotor blades 107 is operably associated with rotor system 105 for creating flight.

Figure 2:
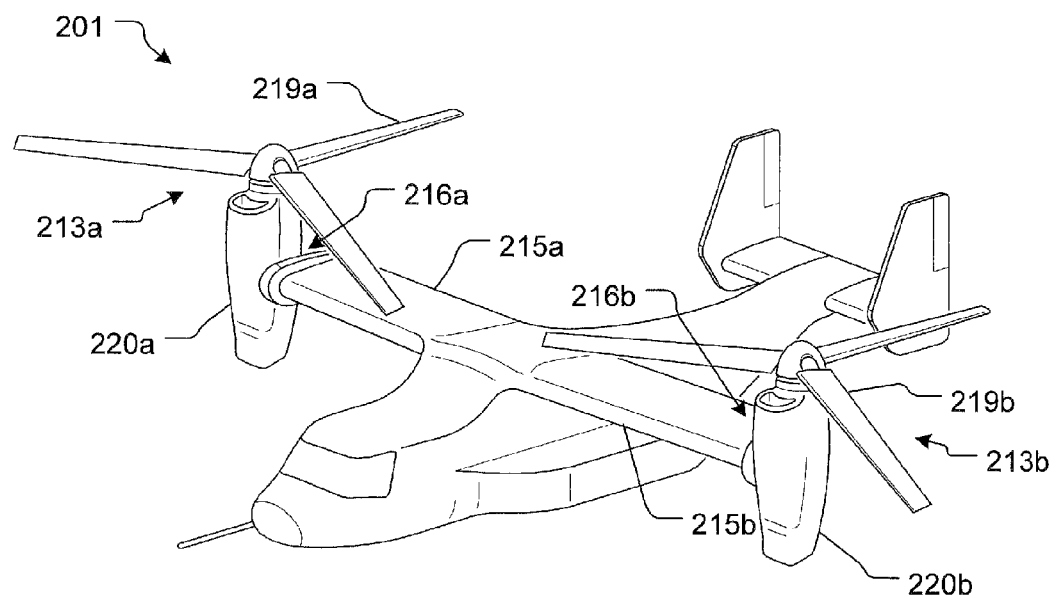
FIG. 2 is a perspective view of a tiltrotor aircraft according to an alternative embodiment of the present application.

Although shown associated with a helicopter, it will be appreciated that the damper system of the present application could also be utilized with different types of rotary aircraft and vehicles. For example, FIG. 2 illustrates a tiltrotor aircraft 201 that utilizes the damper system in accordance with the present application.

Tiltrotor aircraft 201 includes rotor assemblies 213*a* and 213*b* that are carried by wings 215*a* and 215*b*, and are disposed at end portions 216*a* and 216*b* of wings 215*a* and 215*b*, respectively. Tilt rotor assemblies 213*a* and 213*b* include nacelles 220*a* and 220*b*, which carry the engines and transmissions of tilt rotor aircraft 201, as well as, rotor proprotors 219*a* and 219*b* on forward ends 221*a* and 221*b* of tilt rotor assemblies 213*a* and 213*b*, respectively. Tilt rotor assemblies 213*a* and 213*b* move or rotate relative to wing members 215*a* and 215*b* between a helicopter mode in which tilt rotor assemblies 213*a* and 213*b* are tilted upward, such that tilt rotor aircraft 201 flies like a conventional helicopter; and an airplane mode in which tilt rotor assemblies 213*a* and 213*b* are tilted forward, such that tilt rotor aircraft 201 flies like a conventional propeller driven aircraft.

Figure 3:
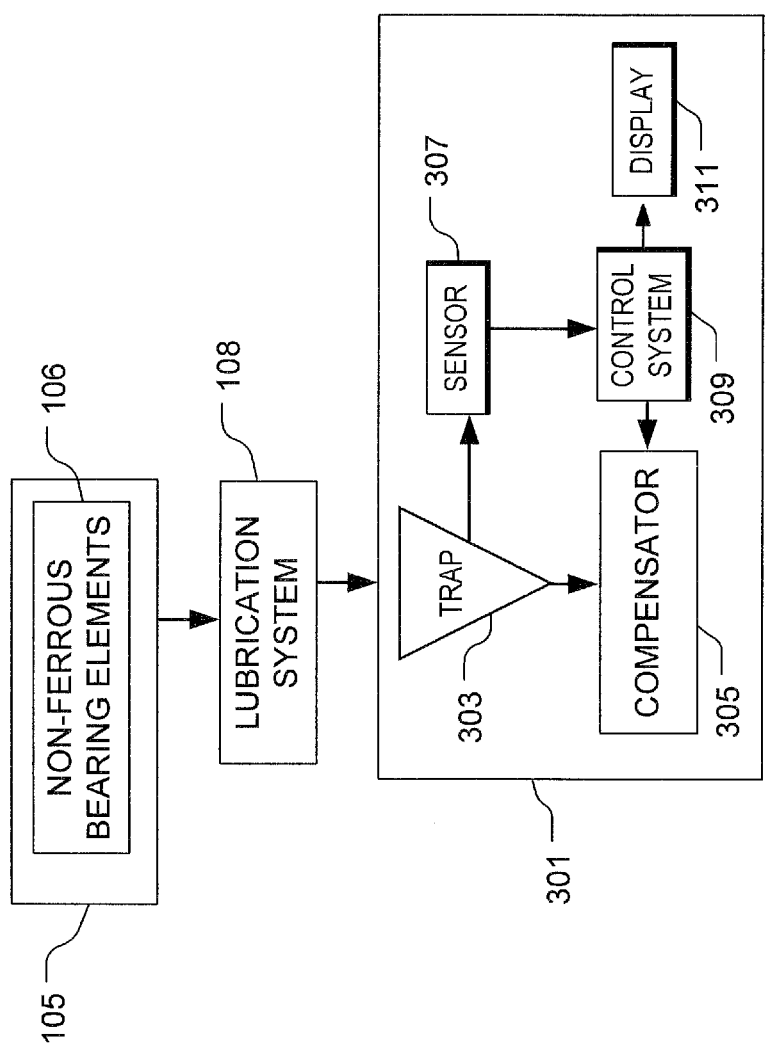
FIG. 3 is a simplified schematic of the debris detection system in accordance with a preferred embodiment of the present application.

FIG. 3 shows a simplified schematic of the debris detection system 301 according to the preferred embodiment of the present application. System 301 includes a trap 303 configured to collect non-ferrous material from one or more non-ferrous roller bearing element 106 operably associated with rotor system 105. To achieve this feature, trap 303 is positioned within the flow of lubrication fluid in communication with the roller bearing element, wherein the fluid passes through the trap while the non-ferrous material is collected. Further detailed description of these features is provided below.

In the contemplated embodiment, the roller bearing element are operably associated with rotor system 105 and the operably associated lubrication system 108; however, system 301 could be utilized on one or more different types of roller elements, e.g., sleeve bearings, needle bearings, components associated with bearing, and the like, in lieu of the preferred embodiment. The roller bearings could be the roller bearing or devices operably associated roller bearing to cause the roller bearing element to fail. It should also be appreciated that system 301 can also be utilized to determine failure of other devices that utilize lubrication systems in lieu of the preferred embodiment.

System 301 preferably includes a compensator 305 operably associated with trap 303. Compensator 305 is configured to compensate for fluid effects exerted on the trap, i.e., fluid pressure, which would otherwise cause a false triggering of non-ferrous debris detection. Further detailed description of these features is provided below.

A sensor 307 is utilized to sense non-ferrous material debris collected by trap 303. The sensed readings from sensor 307 are relayed to a control system 309, which in turn provides notification via an indicator 311, e.g., a monitor or display means, to the user.

Figure 4:
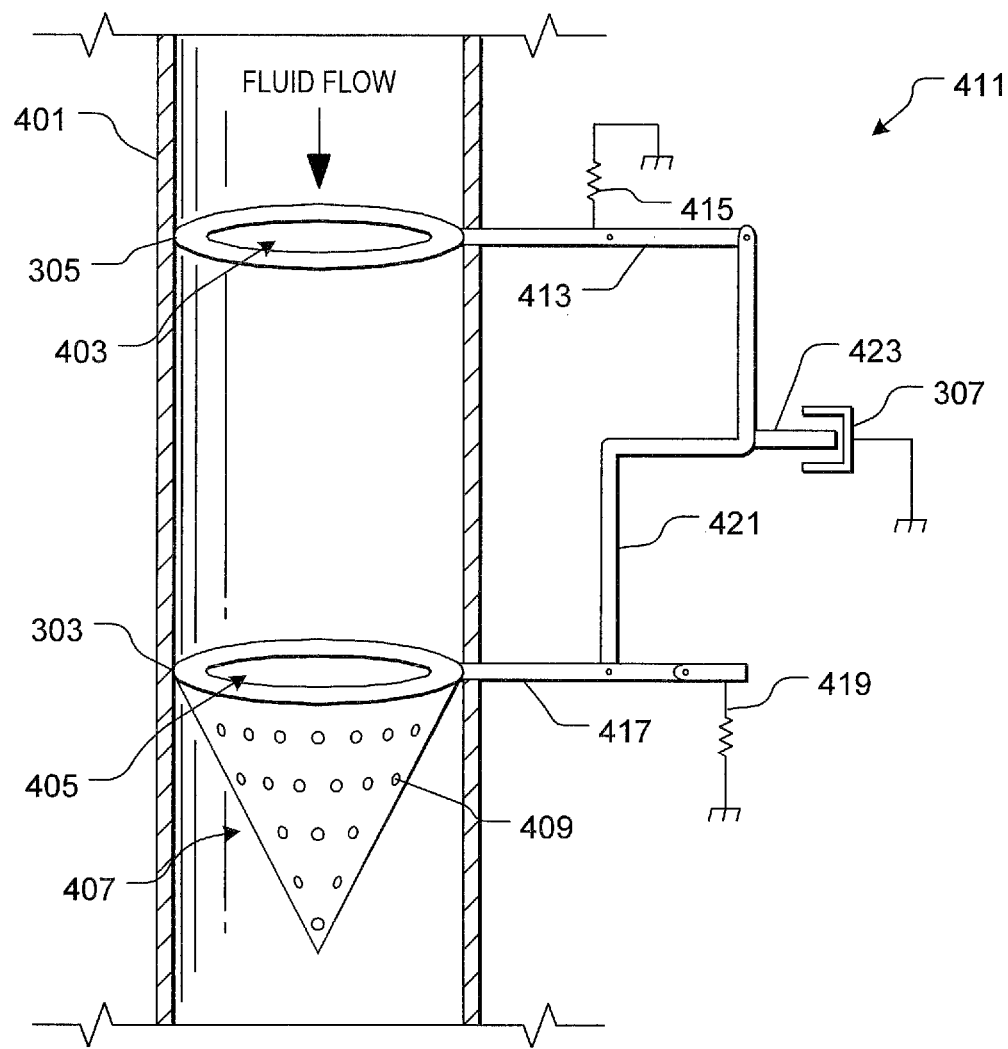
FIG. 4 is a front view of the debris detection system in accordance with the preferred embodiment of the present application.

FIG. 4 is a front view of system 301 operably associated with a conduit 401 of lubrication system 108. Conduit 401 is configured to channel fluid from the roller bearing element to a lubrication pump (not shown) of system 108. As shown, both trap 303 and compensator 305 are positioned within conduit 401 and are both in fluid communication with the lubrication fluid passing therethrough.

Compensator 305 includes an orifice 403 that creates an opening for fluid passage therethrough, and in the contemplated embodiment, orifice 403 is preferably fixed in diameter; however, alternative embodiments could include an orifice that changes in diameter "D" autonomously or manually (see, FIG. 5), thereby regulating fluid flow.

Trap 303 includes an orifice 405 and a perforated strainer 407. During use, the lubrication fluid passes through both the orifice 405 and through the strainer 407. In the contemplated embodiment, strainer 407 includes a plurality of holes 409 selectively tailored in size to trap non-ferrous materials from the roller bearing elements. Thus, strainer 407 is configured to allow passage of lubrication fluid while trapping the non-ferrous material debris from the roller bearing element.

System 301 is also preferably provided with a linkage system 411 operably associate with compensator 305, trap 303, and sensor 307. In the contemplated embodiment, linkage system 411 includes three links: a first link 413 attached to compensator 305 and grounded with a first spring 415; a second link 417 attached to trap 303 and grounded with a second spring 419; and a third link 421 that pivotally connects with both the first link 413 to the second link 417. A lever 423 is attached to third link 421 for creating contact with sensor 307 as trap 303 pivots due to debris collection.

Linkage system 411 is configured to compensate for various fluid flow pressures via the compensator 305 as fluid passes through conduit 401. As shown, movement of compensator 305 pivots link 413, which in turn pivots link 417 and trap 303 when fluid pressure is applied thereagainst without causing sensor 307 to trigger. Non-ferrous material trapped within trap 303 causes the imbalance between the compensator and trap, resulting in link 417 pivoting and thereafter triggering of sensor 307 via lever 423.

Figure 5:
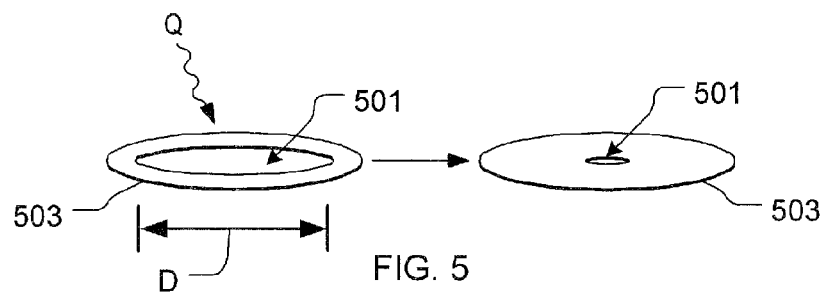
FIGS. 5 and 6 are perspective views of a compensator of the debris detection system of FIG. 4.
Figure 6:
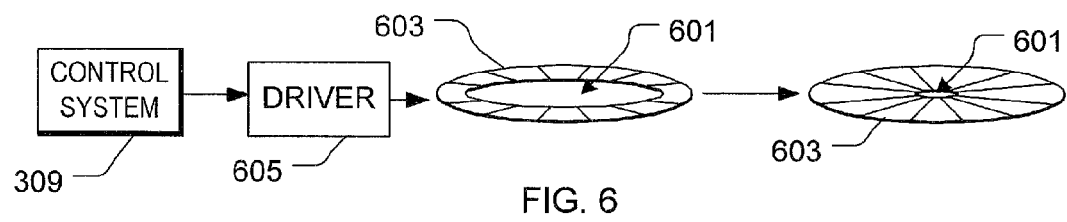

FIGS. 5 and 6 illustrate two alternative embodiments of compensator 305. In the first embodiment, an orifice 501 of a compensator 503 changes in diameter "D" as heat "Q" is applied thereagainst. Thus, compensator 503 is contemplated having material properties that changes the orifice opening as heat is applied thereagainst. This feature allows controlling of fluid passage through the orifice when changing fluid temperatures.

FIG. 6 illustrates a compensator 601 operably associated with control system 309. In this embodiment, the diameter of orifice 603 is either manually or autonomously controlled by a driver 605 controlled by control system 309.

It will be appreciated that the features of compensators 601 and 503 could easily be incorporated in system 301.

Figure 7:
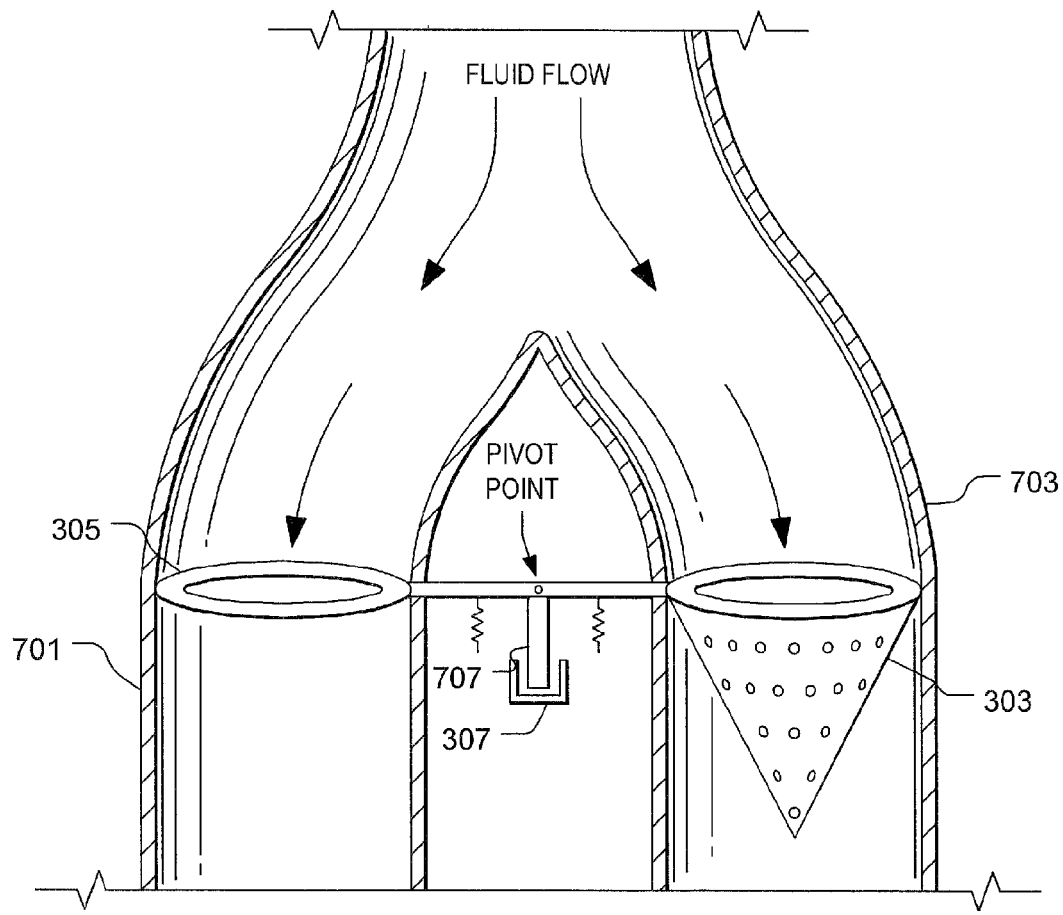
FIGS. 7 and 8 are front views of alternative embodiments of the debris detection system.
Figure 8:
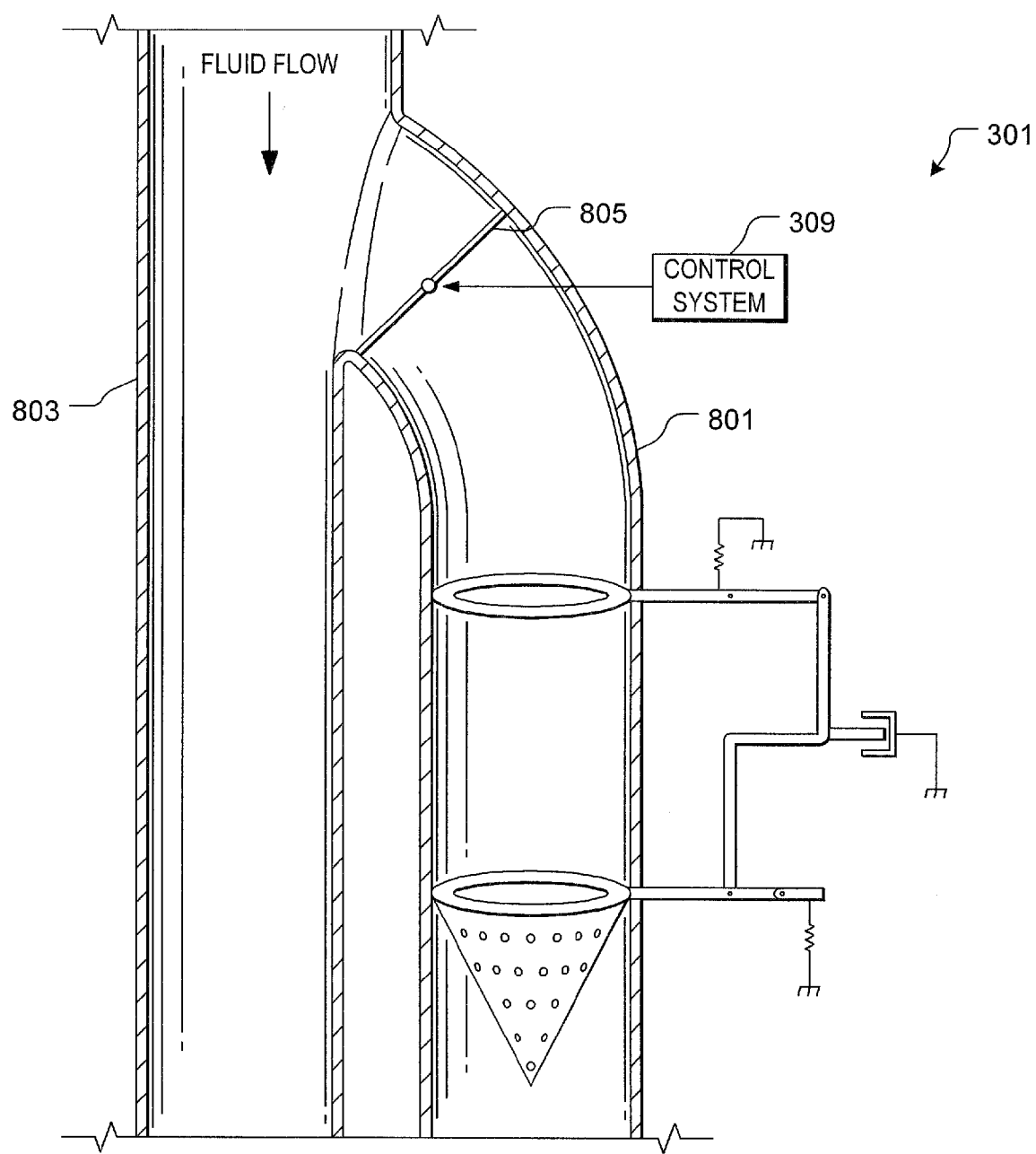

FIGS. 7 and 8 are front views of alternative embodiments of debris detection system 301. In FIG. 7, system 301 is configured to facilitate a lubrication system having a conduit that bifurcates into a first conduit 701 and a second conduit 703. As shown, compensator 305 is positioned in first conduit 701 while trap 303 is positioned in second conduit 703. In this embodiment, a single link 705 is utilized to attach trap 303 to compensator 305. A lever 707 attached to link 705 is used to trigger sensor 307 as non-ferrous material is trapped within trap 303.

It will also be appreciated that system 301 could be utilized in lubrication systems having bypass conduits. In FIG. 8, system 301 is shown operably associated with a bypass conduit 801 in fluid communication with a primary conduit 803. Fluid is restricted from entering bypass conduit 801 with a bypass valve 805 positioned upstream of system 301. In the contemplated embodiment, valve 805 is operably associated with control system 309, which allows selective sampling of the fluid during use. Thus, during operation, the control system 309 activates valve 805 to allow passage of the fluid through conduit 801 for testing. Thereafter, the valve 805 closes access to conduit 801.

It is apparent that a system and method with significant advantages has been described and illustrated. The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A system to detect non-ferrous material debris of a damaged roller bearing element, the system comprising:
a trap in fluid communication with a lubrication fluid of the roller bearing element, the trap having a body with a plurality of openings extending through a thickness of the body;
wherein the openings provide fluid passage therethrough;
a compensator operably associated with the trap; and
a sensor operably associate with the trap;
wherein the trap is configured to collect the non-ferrous material debris while allowing passage of the lubrication fluid;
wherein the compensator pivots;
wherein the trap is configured to pivot due to non-ferrous debris collection; and
wherein the sensor is triggered by the trap pivoting upon detection of the non-ferrous material debris collected by the trap.

2. The system of claim 1,
wherein the compensator is configured to compensate for lubrication fluid pressure by pivoting.

3. The system of claim 2, the compensator comprising:
an orifice configured to allow fluid passage therethrough.

4. The system of claim 3, wherein the orifice is configured to change in opening size to restrict fluid passage therethrough.

5. The system of claim 4, wherein the orifice is composed of a material that expands as heat is applied thereagainst, thus changing the opening size of the orifice to restrict fluid passage therethrough.

6. The system of claim 4, further comprising:
a control system; and
a driver operably associated with the orifice;
wherein the control system commands the driver to change the opening size of the orifice.

7. The system of claim 1, further comprising:
a linkage system operably associated with the trap and the sensor;
wherein the linkage system triggers the sensor as the non-ferrous material debris is trapped in the trap.

8. The system of claim 7, further comprising:
the compensator operably associated with the trap and linkage system;
wherein the compensator is configured to compensate for lubrication fluid pressure; and
wherein the linkage system is configured to pivot the trap with pivoting movement of the compensator.

9. The system of claim 8, the linkage system comprising:
a first link attached to the compensator;
a second link attached to the trap; and
a third link configured to join the first link and the second link, the third link having a lever configured to trigger the sensor with pivoting movement of the trap.

10. The system of claim 8, the linkage system comprising:
a link attached to both the trap and the compensator, the link having a lever that triggers the sensor with pivoting movement of the trap.

11. The system of claim 1, further comprising:
a bypass valve positioned upstream of the trap;
wherein the bypass valve restricts lubrication fluid from passing through the trap.

12. The system of claim 11, further comprising:
a control system operably associated with the bypass valve;
wherein the control system is configured to open and close the bypass valve, thereby allowing lubrication fluid to pass through the trap.

13. The system of claim 1, further comprising:
a control system operably associated with the sensor.

14. The system of claim 13, further comprising:
an indicator operably associated with the control system and configured to indicate whether non-ferrous material debris is collected by the trap.

15. The system of claim 1, the trap comprising:
an orifice configured for fluid passage;
a perforated strainer configured to receive the lubrication fluid passing through the orifice and configured to trap the non-ferrous material debris.

16. An aircraft, comprising:
a rotor system having a non-ferrous bearing;
a lubrication system configured to lubricate the non-ferrous bearing with a lubrication fluid;
a non-ferrous material debris detection system, having:
a trap in fluid communication with a lubrication fluid, the trap having a body with a plurality of openings extending through a thickness of the body;
wherein the openings provide fluid passage therethrough; and
a sensor operably associated with the trap, the sensor configured to detect motion of the trap;
wherein the trap is configured to collect the non-ferrous material debris in the lubrication fluid;
wherein the trap is configured to pivot due to non-ferrous debris collection; and
wherein the sensor is triggered by the trap pivoting upon detection of the non-ferrous material debris collected by the trap.

17. The aircraft of claim 16, further comprising:
a linkage system operably associated with the trap and the sensor;
wherein the linkage system triggers the sensor as the non-ferrous material debris is collected in the trap.

18. The aircraft of claim 16, further comprising:
a control system operably associated with the sensor; and
an indicator operably associated with the control system and configured to indicate whether non-ferrous material debris is trapped in the trap.

* * * * *